United States Patent [19]
Sauer et al.

[11] Patent Number: 5,508,383
[45] Date of Patent: Apr. 16, 1996

[54] CYCLIC PEPTIDE LHRH ANTAGONISTS

[75] Inventors: Daryl R. Sauer, Gurnee; Fortuna Haviv, Deerfield, both of Ill.

[73] Assignee: Tap Holdings Inc., Deerfield, Ill.

[21] Appl. No.: 208,544

[22] Filed: Mar. 9, 1994

[51] Int. Cl.$^6$ .............. C07K 14/59; C07K 7/64
[52] U.S. Cl. .............. 530/313; 530/317; 530/328
[58] Field of Search .............. 514/11, 9, 15, 514/2, 800; 530/313, 317, 328

[56] References Cited

U.S. PATENT DOCUMENTS

| | | | |
|---|---|---|---|
| 5,110,904 | 5/1992 | Haviv et al. | 530/313 |
| 5,300,492 | 4/1994 | Haviv et al. | 530/313 |

FOREIGN PATENT DOCUMENTS

WO91/12013  8/2291  WIPO.

OTHER PUBLICATIONS

J. Rivier, et al., Proceedings of the Ninth American Peptide Symposium Pierce Chemical Co., Rockford, IL 541–544, 1985.

R. M. Freidinger, et al., Proceedings of the Ninth American Peptide Symposium, Pierce Chemical Co., Rockford, IL 549–552, 1985.

J. Rivier, et al., J. Med. Chem. 31(3): 677–682 (1988).

A. S. Dutta, et al., Biochem. and Biophys. Res. Comm. 159(3): 1114–1120 (1989).

J. Rivier, et al., Proceedings of the 11th American Peptide Symposium 33–37 (1990).

R. S. Struthers, Proteins: Structure, Function, and Genetics, 8:295–304 (1990).

J. Rizo, et al., J. Am. Chem. Soc. 114(8):2852–2859 (1992).

J. Rivier, et al., Contraception 46:109–112 (1992).

R. J. Bienstock, et al., J. Med. Chem. 36:3265–3273 (1993).

A. S. Dutta, et al., Bioorganic and Med. Chem. Letters 3(5):943–948 (1993).

*Primary Examiner*—Christina Y. Chan
*Assistant Examiner*—T. D. Wessendorf
*Attorney, Agent, or Firm*—Jerry F. Janssen

[57] ABSTRACT

A class of cyclic peptides are effective inhibitors of LHRH and are useful in the treatment of disease conditions which are mediated by sex hormones including prostate cancer, endometriosis, uterine fibroids, and precocious puberty.

1 Claim, No Drawings

CYCLIC PEPTIDE LHRH ANTAGONISTS

TECHNICAL FIELD

The present invention relates to organic compounds having biological activity, to compositions containing those compounds, and to a method for their use. More particularly, the present invention concerns a class of cyclic peptides which are antagonists of LHRH, to pharmaceutical compositions containing those cyclic peptides, and to a method of treatment employing the compounds and compositions.

BACKGROUND OF THE INVENTION

The gonadotropins: follicle stimulating hormone (FSH), luteinizing hormone (LH), and chorionic gonadotropin (CG), are required for ovulation, spermatogenesis, and the biosynthesis of sex steroids. A single hypothalamic hormone, gonadotropin-releasing hormone (GnRH, also known as luteinizing hormone-releasing hormone, (LHRH) is responsible for regulating the secretion of both FSH and LH in mammals. Early attempts to prepare peptides having LHRH-like activity centered on the synthesis of compounds which were LHRH agonists. However, in 1976 it was found that while individual does of LHRH stimulated the release of gonadotropins, the continuous administration of small doses of LHRH or chronic administration of LHRH agonists had the opposite effect. This finding stimulated research for the discovery of both agonist and antagonist analogs of LHRH as agents useful for regulating sex steroids in mammals. A considerable number of patents and articles in the open literature disclose analogs of LHRH which either act as agonists of LHRH (i.e. act to stimulate the release of LH and FSH) or as antagonists of LHRH (i.e. act to inhibit the release of LH and FSH). For the most part, these compounds contain nine or ten aminoacyl residues, substituting naturally-occurring or non-naturally-occurring amino acid residues at one or more positions in the natural sequence of LHRH. In some cases, active antagonists of LHRH have been reported which contain fewer than ten amino acid residues.

The literature has reported that LHRH antagonists are useful for the treatment of a variety of conditions in which the suppression of sex steroids plays a key role including contraception, delay of puberty, treatment of benign prostatic hyperplasia, palliative treatment or remission of hormonal-dependent tumors of the breast and ovaries, palliative treatment or remission of hormonal-dependent tumors of the prostate, the treatment of cryptoorchidism, hirsutism in women, gastric motility disorders, dysmenorrhea, and endometriosis.

SUMMARY OF THE INVENTION

The present invention provides, in its principle embodiment, a class of cyclic peptide antagonists of LHRH having the structure:

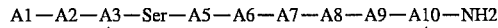

or a pharmaceutically acceptable salt thereof wherein A1 is absent or is am aminoacyl residue selected from the group consisting of N-acetyl-D-3-(naphth-2-yl)alanyl (NAcD2Nal); N-acetyl-D-3-(quinolin-3-yl)alanyl (NAcD3Qal); N-acetyl-D-3-(4-chlorophenyl)alanyl (NAcD4ClPhe); N-acetyl-D-phenylalanyl (NAcDPhe); and N-acetyl-3-(naphth-1-yl)alanyl (NAcD1Nal).

The aminoacyl residue A2 is selected from the group consisting of D4ClPhe; D2Nal; DPhe; and D-3-(4-fluorophenyl)alanyl (D4FPhe).

A3 is selected from the group consisting of L-lysyl (Lys); D-lysyl (DLys); L-ornithyl (Orn); D-ornithyl (DOrn); D-glutamyl (DGlu,); L-glutamyl (Glu); D-homolysyl (i.e. 2,7-diaminoheptanoic acid, D-HLys); D-2,3-diaminopropionyl (DDap); D-homoglutamyl (i.e. 2-amino-5-aminopentanoic acid, DHGlu); and D-aspartyl (DAsp).

A5 is selected from the group consisting of L-tyrosyl (Tyr); $N^\alpha$-methyl-L-tyrosyl (NMeTyr); L-arginyl (Arg); L-3-(4-(3-amino-1,2,4-triazol-5-yl)phenyl)alanyl (PheAtz); L-phenylalanyl (Phe); L-tyrosyl-O-methyl (TyrOMe); L-lysyl(N-epsilon-nicotinyl) (LysNic); L-lysyl-N-epsilon-picolyl) (Lys(Pic); and L-2-aminoguanidinohexanoic acid (HArg).

A6 is selected from the group consisting of DLys(Nic); D-lysyl(N-epsilon-pyrazinyl) (DLys(Pyz); D-lysyl(N-epsilon(nicotinylglycyl) (DLys(GlyNic); DPhe(Atz), D-citrullyl (DCit); D-homocitrullyl (I.e. 2-amino-6-ureidohexanoic acid, DHcit); D-lysyl(N-epsilon(6-aminonicotinyl) (DLys(6ANic), D-Lysyl(N-epsilon(azaglyclnicotinyl) (DLys(AzaglyNic); D-lysyl(N-epsilon(azaglycyl-2-furoyl)) (DLysAzaGlyFurl); D-ornithyl(N-delta(6-aminonicotinyl)) (DOrn(6ANic); and D-2-amino- 6-$N^G$,$N^G$-diethylguanidinohexanoic acid (DHArg(Et$_2$)).

A7 is selected from the group consisting of L-leucyl (Leu); $N^\alpha$-methyl L-leucyl (NMeLeu); L-isoleucyl (Ile); and L-valyl (Val).

A8 is selected from the group consisting of L-lylsyl(n-epsilon-isopropyl) (Lys(Isp)); Arg; Hcit; HArg; and HArg(Et2).

A9 is selected from the group consisting of L-prolyl (Pro), $N^\alpha$-methylalanyl (NMeAla); glycyl (Gly); and sarcosyl (Sar).

A10 is selected from the group consisting of DGlu; Glu; Lys; DLys; Orn; DOrn; DHLys, DDap, DHGlu, and DAsp.

In the above-identified aminoacyl sequences, when the aminoacyl residue designated A1 is absent then A2 is selected from the group consisting of acetyl; phenylacetyl, 3-phenylpropionyl,3-(4-fluorophenyl)propionyl,3-(4-chlorophenyl)propionyl, and 4-fluorophenylacetyl.

In another embodiment of the present invention there are provided pharmaceutical formulations for use in suppressing levels of sex hormones in a mammal comprising a sex hormone suppressing effective amount of a compound as defined above in combination with a pharmaceutically acceptable carrier.

In yet another embodiment of the present invention there is provided a method of suppressing levels of sex hormones in a mammal comprising administering to a mammal in need of such treatment a therapeutically effective amount of a compound as defined above.

DETAILED DESCRIPTION

As used throughout this specification and the amended claims, the terms "resin" or "peptide resin" as used herein refer to resins of the type commonly used in the art of synthetic peptide preparation. Examples of such resins include, but are not limited to, methyl benzhydrylamine (MBHA) or benzhydrylamine (BHA).

Unless indicated otherwise by a "D" prefix, the stereochemistry of the alpha-carbon atom of the amino acids and aminoacyl residues in peptides described in this specification and the appended claims is the natural or "L" configuration.

For the most part, the names of naturally-occuring and non-naturally-occuring aminoacyl residues used herein follow the naming conventions suggested by the IUPAC Commission on the Nomenclature of Organic Chemistry and the IUPAC-IUB Commission on Biochemical Nomenclature as set out in "Nomenclature of α-Amino Acids (Recommendations, 1974)," *Biochemistry*, 14(2): 1975). It is to be noted that throughout this specification and the appended claims, the term "glutamyl" refers to an aminoacyl residue derived from glutamic acid, while the term "glutaminyl" denotes an aminoacyl residue derived from glutamine.

To the extent that the names and abbreviations of amino acids and aminoacyl residues employed in this specification and appended claims differ from those suggestions, they will be made clear to the reader by the definitions given above in the "Summary of the Invention" section.

Throughout this specification and the appended claims, when a peptide is names by using a linear representation of aminoacyl residue abbreviations, the cyclized portion of the peptide is enclosed within braces and the bracketed aminoacyl residues linked in the cyclized peptide are preceded by a lower case italicized letter "*c.*" For example, "Ac-D2Nal-D4ClPhe-*c*-{ DLys-Ser-NMeTyr-DLys(Nicotinyl)-Leu-Lys(N-epsilon-Isopropyl-Pro-DGlu}-NH$_2$" indicates a cyclic decapeptide wherein the side chain of the lysyl residue at position 3 is linked to the D-glutamyl residue at position 10 by a peptide bond.

By the term "pharmaceutically acceptable salt" is meant salts recognized in the pharmaceutical formulation arts as non-toxic and suitable for use in formulations intended for use in human and animal treatment. Suitable acids and bases useful for this purpose are listed, for example, in the review article, "Pharmaceutical Salts" by S. N. Berge, et al., *J. Pharm. Sci.*, 66: 1–19 (1977).

Representative examples of compounds contemplated as falling within the scope of the present invention include, but are not limited to the following:

Ac-D2Nal-D4ClPhe-*c*-{DLys-Ser-NMeTyr-DLys)Nicotinyl)-Leu-Lys(N-epsilon-Isopropyl-Pro-DGlu}-NH$_2$;
Ac-D2Nal-D4ClPhe-*c*-{DLys-Ser-Tyr-DLys(Nicotinyl)-Leu-Lys(N-epsilon-Isopropyl-Pro-Glu}-NH$_2$;
Ac-D2Nal-D4ClPhe-*c*-{Lys-Ser-NMeTyr-DLys(Nicotinyl)-Leu-Lys(N-epsilon-Isopropyl)-Pro-DGlu}-NH$_2$;
Ac-D2Nal-D4ClPhe-*c*-{DLys-Ser-NMeTyr-DLys(Nicotinyl)-Leu-Lys(N-epsilon-Isopropyl)-Pro-Glu}-NH$_2$;
Ac-D2Nal-D4ClPhe-*c*-{Lys-Ser-NMeTyr-DLys(Nicotinyl)-Leu-Lys(N-epsilon-Isopropyl)-Pro-Glu}-NH$_2$;
Ac-D2Nal-D4ClPhe-*c*-{Glu-Ser-NMeTyr-DLys(Nicotinyl)-Leu-Lys(N-epsilon-Isopropyl)-Pro-DOrn}-NH$_2$;
Ac-D2Nal-D4ClPhe-*c*-{DGlu-Ser-NMeTyr-DLys(Nicotinyl)-Leu-Lys(N-epsilon-Isopropyl)-Pro-DLys)}-NH$_2$;
Ac-D2Nal-D4ClPhe-*c*-{DLys-Ser-Tyr-DLys(Nicotinyl)-Leu-Lys(N-epsilon-Isopropyl)-Pro-DGlu}-NH$_2$;
Ac-*c*-{DLys-Ser-NMeTyr-DLys(Nicotinyl)-Leu-Lys(N-epsilon-Isopropyl)Pro-DGlu}-NH$_2$;
4FPhenylacetyl-*c*-{DLys-Ser-NMeTyr-DLys(Nicotinyl)-Leu-Lys(N-epsilon-Isopropyl)-Pro-DGlu}-NH$_2$;
Ac-*c*-{DGlu-Ser-NMeTyr-DLys(Nicotinyl)-Leu-Lys(N-epsilon-Isopropyl-Pro-DLys}-NH$_2$;
Ac-D2Nal-D4ClPhe-*c*-{DGlu-Ser-NMeTyr-DLys(Nicotinyl)-Leu-Lys(N-epsilon-Isopropyl)-Pro-Lys}-NH$_2$;
4ClPhenylpropionyl-*c*-{DLys-Ser-NMeTyr-DLys(Nicotinyl)-Leu-Lys(N-epsilon-Isopropyl)-Pro-DGlu}-NH$_2$;
Ac-D2Nal-D4ClPhe-*c*-{DOrn-Ser-NMeTyr-DLys(Nicotinyl)-Leu-Lys(N-epsilon-Isopropyl)-Pro-DGlu}-NH$_2$;
4FPhenylacetyl-*c*-{DGlu-Ser-NMeTyr-DLys(Nicotinyl)-Leu-Lys(N-epsilon-Isopropyl)-Pro-DLys}-NH$_2$;
4ClPhenylpropionyl-*c*-{DLys-Ser-NMeTyr-DLys(Nicotinyl)-Leu-Lys(N-epsilon-Isopropyl)-Gly-DGlu}-NH$_2$;
NAc-D2Nal_D4ClPhe-*c*-{DLys-Gly-NMeTyr-DLys(Nicotinyl)-Leu-Lys(N-epsilon-Isopropyl)-Gly-DGlu}-NH$_2$;
4ClPhepropionyl-*c*-{DLys-Gly-NMeTyr-DLys(Nicotinyl)-Leu-Lys(N-epsilon-Isopropyl)-Gly-DGlu}-NH$_2$;
NAc-*c*-{DGlu-Gly-NMeTyr-DLys(Nicotinyl)-Leu-Lys(N-epsilon-Isopropyl)-Sar-DLys}-NH$_2$;
Ac-D2Nal-D4ClPhe-*c*-{DHLys-Ser-NMeTyr-DLys(Nicotinyl)-Leu-Lys(N-epsilon-Isopropyl)-Pro-DAsp}-NH$_2$;
Ac-D2Nal-D4ClPhe-*c*-{DHLys-Ser-NMeTyr-DLys(Nicotinyl)-Leu-Lys(N-epsilon-Isopropyl)-Pro-DGlu}-NH$_2$;
Ac-D2Nal-D4ClPhe-*c*-{DHLys-Ser-NMeTyr-DLys(Nicotinyl)-Leu-Lys(N-epsilon-Isopropyl)-Pro-DHGlu}-NH$_2$;
Ac-D2Nal-D4ClPhe-*c*-{DDap-Ser-NMeTyr-DLys(Nicotinyl)-Leu-Lys(N-epsilon-Isopropyl)-Pro-DAsp}-NH$_2$;
Ac-D2Nal-D4ClPhe-*c*-{DDap-Ser-NMeTyr-DLys(Nicotinyl)-Leu-Lys(N-epsilon-Isopropyl)-Pro-DGlu}-NH$_2$;
Ac-D2Nal-D4ClPhe-*c*-{DDap-Ser-NMeTyr-DLys(Nicotinyl)-Leu-Lys(N-epsilon-Isopropyl)-Pro-DHGlu}-NH$_2$;
Ac-D2Nal-D4ClPhe-*c*-{DLys-Ser-NMeTyr-DLys(Nicotinyl)-Leu-Lys(N-epsilon-Isopropyl-Pro-DAsp}-NH$_2$;
Ac-D2Nal-D4ClPhe-*c*-{DLys-Ser-NMeTyr-DLys(Nicotinyl)-Leu-Lys(N-epsilon-Isopropyl)-Pro-DHGlu}-NH$_2$;
Ac-D2Nal-D4ClPhe-*c*-{DOrn-Ser-NMeTyr-DLys(Nicotinyl)-Leu-Lys(N-epsilon-Isopropyl)-Pro-DAsp}-NH$_2$;
Ac-D2Nal-D4ClPhe-*c*-{DOrn-Ser-NMeTyr-DLys(Nicotinyl)-Leu-Lys(N-epsilon-Isopropyl)-Pro-DHGlu}-NH$_2$;
Ac-D2Nal-D4ClPhe-*c*-{DGlu-Ser-NMeTyr-DLys(Nicotinyl)-Leu-Lys(N-epsilon-Isopropyl)-Pro-DHLys}-NH$_2$;
Ac-D2Nal-D4ClPhe-*c*-{DHGlu-Ser-NMeTyr-DLys(Nicotinyl)-Leu-Lys(N-epsilon-Isopropyl)-Pro-DHLys}-NH$_2$;
Ac-D2Nal-D4ClPhe-*c*-{DAsp-Ser-NMeTyr-DLys(Nicotinyl)-Leu-Lys(N-epsilon-Isopropyl)-Pro-DHLys}-NH$_2$;
Ac-D2Nal-D4ClPhe-*c*-{DGlu-Ser-NMeTyr-DLys(Nicotinyl)-Leu-Lys(N-epsilon-Isopropyl)-Pro-DDap}-NH$_2$;
Ac-D2Nal-D4ClPhe-*c*-{DHGlu-Ser-NMeTyr-DLys(Nicotinyl)-Leu-Lys(N-epsilon-Isopropyl)-Pro-DDap}-NH$_2$;
Ac-D2Nal-D4ClPhe-*c*-{DAsp-Ser-NMeTyr-DLys(Nicotinyl)-Leu-Lys(N-epsilon-Isopropyl)-Pro-DDap}-NH$_2$;
Ac-D2Nal-D4ClPhe-*c*-{DGlu-Ser-NMeTyr-DLys(Nicotinyl)-Leu-Lys(N-epsilon-Isopropyl)-Pro-DOrn}-NH$_2$;
Ac-D2Nal-D4ClPhe-*c*-{DHGlu-Ser-NMeTyr-DLys(Nicotinyl)-Leu-Lys(N-epsilon-Isopropyl)-Pro-DOrn}-NH$_2$;
Ac-D2Nal-D4ClPhe-*c*-{DAsp-Ser-NMeTyr-DLys(Nicotinyl)-Leu-Lys(N-epsilon-Isopropyl)-Pro-DOrn}-NH$_2$;
Ac-D2Nal-D4ClPhe-*c*-{DHGlu-Ser-NMeTyr-DLys(Nicotinyl)-Leu-Lys(N-epsilon-Isopropyl)-Pro-D-Lys}-NH$_2$;
Ac-D2Nal-D4ClPhe-*c*-{DAsp-Ser-NMeTyr-DLys(Nicotinyl)-Leu-Lys(N-epsilon-Isopropyl)-Pro-D-Lys}-NH$_2$;
Ac-D3Qal-D4ClPhe-*c*-{DLys-Ser-NMeTyr-DLys(Nicotinyl)-Leu-Lys(N-epsilon-Isopropyl)-Pro-DGlu}-NH$_2$;
Ac-D4ClPhe-D4ClPhe-*c*-{DLys-Ser-NMeTyr-DLys(Nicotinyl)-Leu-Lys(N-epsilon-Isopropyl)-Pro-DGlu}-NH$_2$;
Ac-DPhe-D4ClPhe-*c*-{DLys-Ser-NMeTyr-DLys(Nicotinyl)-Leu-Lys(N-epsilon-Isopropyl)-Pro-DGlu}-NH$_2$;
Ac-D1-Nal-D4ClPhe-*c*-{DLys-Ser-NMeTyr-DLys(Nicotinyl)-Leu-Lys(N-epsilon-Isopropyl)-Pro-DGlu}-NH$_2$;
Ac-D2Nal-DPhe-*c*-{DLys-Ser-NMeTyr-DLys(Nicotinyl)-Leu-Lys(N-epsilon-Isopropyl)-Pro-DGlu}-NH$_2$;
Ac-D3Qal-DPhe-*c*-{DLys-Ser-NMeTyr-DLys(Nicotinyl)-Leu-Lys(N-epsilon-Isopropyl)-Pro-DGlu}-NH$_2$;
Ac-D4-ClPhe-DPhe-*c*-{DLys-Ser-NMeTyr-DLys(Nicotinyl)-Leu-Lys(N-epsilon-Isopropyl)-Pro-DGlu}-NH$_2$;
Ac-DPhe-DPhe-*c*-{DLys-Ser-NMeTyr-DLys(Nicotinyl)-Leu-Lys(N-epsilon-Isopropyl)-Pro-DGlu}-NH$_2$;
AC-D1-Nal-DPhe-*c*-{DLys-Ser-NMeTyr-DLys(Nicotinyl)-Leu-Lys(N-epsilon-Isopropyl)-Pro-DGlu}-NH$_2$;

Ac-D2-Nal-D2-Nal-c-{DLys-Ser-NMeTyr-DLys(Nicotinyl)-Leu-Lys(N-epsilon-Isopropyl)-Pro-DGlu}-NH₂;
Ac-D3Qal-D2Nal-c-{DLys-Ser-NMeTyr-DLys(Nicotinyl)-Leu-Lys(N-epsilon-Isopropyl)-Pro-DGlu}-NH₂;
Ac-D4ClPhe-D2Nal-c-{DLys-Ser-NMeTyr-DLys(Nicotinyl)-Leu-Lys(N-epsilon-Isopropyl)-Pro-DGlu}-NH₂;
Ac-DPhe-D2-Nal-c-{DLys-Ser-NMeTyr-DLys(Nicotinyl)-Leu-Lys(N-epsilon-Isopropyl)-Pro-DGlu}-NH₂
Ac-D1Nal-D2Nal-c{DLys-Ser-NMeTyr-DLys(Nicotinyl)-Leu-Lys(N-epsilon-Isopropyl)-Pro-DGlu}-NH₂;
Ac-D2-Nal-D4FPhe-c-{DLys-Ser-NMeTyr-DLys(Nicotinyl)-Leu-Lys(N-epsilon-Isopropyl)-Pro-DGlu}-NH₂
Ac-D3Qal-D4FPhe-c-{DLys-Ser-NMeTyr-DLys(Nicotinyl)-Leu-Lys(N-epsilon-Isopropyl)-Pro-DGlu}-NH₂;
Ac-D4ClPhe-D4FPhe-c-{DLys-Ser-NMeTyr-DLys(Nicotinyl)-Leu-Lys(N-epsilon-Isopropyl)-Pro-DGlu}-NH₂;
Ac-DPhe-D4FPhe-c-{DLys-Ser-NMeTyr-DLys(Nicotinyl)-Leu-Lys(N-epsilon-Isopropyl)-Pro-DGlu}-NH₂;
Ac-D1Nal-D4FPhe-c-{DLys-Ser-NMeTyr-DLys(Nicotinyl)-Leu-Lys(N-epsilon-Isopropyl)-Pro-DGlu}-NH₂;
Ac-D2Nal-D4ClPhe-c-{DLys-Ser-Arg-DLys(Nicotinyl)-Leu-Lys(N-epsilon-Isopropyl)-Pro-DGlu}-NH₂;
Ac-D2Nal-D4ClPhe-c-{DLys-Ser-Phe-DLys(Nicotinyl)-Leu-Lys(N-epsilon-Isopropyl)-Pro-DGlu}-NH₂;
Ac-D2Nal-D4ClPhe-c-{DLys-Ser-Tyr(OMe)-DLys(Nicotinyl)-Leu-Lys(N-epsilon-Isopropyl)-Pro-DGlu}-NH₂;
Ac-D2Nal-D4ClPhe-c-{DLys-Ser-Lys(Nic)-DLys(Nicotinyl)-Leu-Lys(N-epsilon-Isopropyl)-Pro-DGlu}-NH₂;
Ac-D2Nal-D4ClPhe-c-{DLys-Ser-Lys(Pic)-DLys(Nicotinyl)-Leu-Lys(N-epsilon-Isopropyl)-Pro-DGlu}-NH₂;
Ac-D2Nal-D4ClPhe-c-{DLys-Ser-NMeTyr-DLys(Pyz)-Leu-Lys(N-epsilon-Isopropyl)-Pro-DGlu}-NH₂;
Ac-D2Nal-D4ClPhe-c-{DLys-Ser-NMeTyr-DLys(GlyNic)-Leu-Lys(N-epsilon-Isopropyl)-Pro-DGlu}-NH₂;
Ac-D2Nal-D4ClPhe-c-{DLys-Ser-NMeTyr-DCit-Leu-Lys(N-epsilon-Isopropyl)-Pro-DGlu}-NH₂;
Ac-D2Nal-D4ClPhe-c-{DLys-Ser-NMeTyr-DHCit-Leu-Lys(N-epsilon-Isopropyl)-Pro-DGlu}-NH₂;
Ac-D2Nal-D4ClPhe-c-{DLys-Ser-NMeTyr-DLys(6ANic)-Leu-Lys(N-epsilon-Isopropyl)-Pro-DGlu}-NH₂;
Ac-D2Nal-D4ClPhe-c-{DLys-Ser-NMeTyr-DHArg(Et₂)-Leu-Lys(N-epsilon-Isopropyl)-Pro-DGlu}-NH₂;
Ac-D2Nal-D4ClPhe-c-{DLys-Ser-NMeTyr-DLys(Nicotinyl)-NMeLeu Lys(N-epsilon-Isopropyl-Pro-DGlu}-NH₂;
Ac-D2Nal-D4ClPhe-c-{DLys-Ser-NMeTyr-DLys(Nicotinyl-ILe-Lys(N-epsilon-Isopropyl)-Pro-DGlu}-NH₂;
Ac-D2Nal-D4ClPhe-c-{DLys-Ser-NMeTyr-DLys(Nicotinyl)-Val-Lys(N-epsilon-Isopropyl)-Pro-DGlu}-NH₂;
Ac-D2Nal-D4ClPhe-c-{DLys-Ser-NMeTyr-DLys(Nicotinyl)-Leu-HArg-Pro-DGlu}-NH₂;
Ac-D2Nal-D4ClPhe-c-{DLys-Ser-NMeTyr-DLys(Nicotinyl)-Leu-HArg(Et₂)-Pro-DGlu}-NH₂;
Ac-D2Nal-D4ClPhe-c-{DLys-Ser-NMeTyr-DLys(Nicotinyl)-Leu-Arg-Pro-DGlu}-NH₂;
Ac-D2Nal-D4ClPhe-c-{DLys-Ser-NMeTyr-DLys(Nicotinyl)-Leu-HCit-Pro-DGlu}-NH₂;
Ac-D2Nal-D4ClPhe-c-{DLys-Ser-NMeTyr-DLys(Nicotinyl)-Leu-Lys(N-epsilon-Isopropyl)-NMeAla-DGlu}-NH₂;
Ac-D2Nal-D4ClPhe-c-{DLys-Ser-NMeTyr-DLys(Nicotinyl)-Leu-Lys(N-epsilon-Isopropyl)-Gly-DGlu}-NH₂;
Ac-D2Nal-D4ClPhe-c-{DLys-Ser-NMeTyr-DLys(Nicotinyl)-Leu-Lys(N-epsilon-Isopropyl)-Sar-DGlu}-NH₂;
Ac-D2Nal-D4ClPhe-c-{DLys-Ser-Phe(Atz)-DLys(Nicotinyl)-Leu-Lys(N-epsilon-Isopropyl)-Pro-DGlu}-NH₂;
Ac-D2Nal-D4ClPhe-c-{DLys-Ser-NMeTyr-DLys(Atz)-Leu Lys(N-epsilon-Isopropyl)-Pro-DGlu}-NH₂;
Ac-D2Nal-D4ClPhe-c-{DLys-Ser-NMePhe(Atz)-DLys(Nicotinyl)-Leu-Lys(N-epsilon-Isopropyl)-Pro-DGlu}-NH₂;
Ac-D-2Nal-D-4ClPhe-c-{DLys-Ser-NMeTyr-DLys(AzaGlyNic)-Leu-Lys(N-epsilon-Isopropyl)-Pro-D-Glu}-NH₂;
Ac-D2Nal-D-4ClPhe-c-{DLys-Ser-NMeTyr-DLys(FurAzaGly)-Leu-Lys(M-epsilon-Isopropyl)-Pro-DGlu}-NH₂.

SYNTHESIS OF THE PEPTIDES OF THE PRESENT INVENTION

In general, the compounds of the present invention are synthesized by techniques known to those skilled in the art as, for example, by so-called "solid phase" peptide synthesis or by usual methods of solution phase chemistry. A summary of available solid phase peptide synthetic techniques may be found in J. M. Stewart and J. D. Young, *Solid Phase Peptide Synthesis*, W. H. Freeman Co., San Francisco, 1963 and J. Meienhofer, *Hormonal Proteins and Peptides*, Vol. 2, p. 46, Academic Press (New York), 1973. For classical solution synthesis see G. Schroder and K. Lupke, *The Peptides*, vol. 1, Academic Pressure (New York), 1965.

In general, these methods comprise the sequential addition of one or more amino acids or suitably protected amino acids to a growing peptide chain bound to a suitable resin. The starting amino acids are commercially available or, where novel in the compounds of this invention, are synthesized by methods detailed below from readily available starting materials.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected is added, and so forth. After all the desired amino acids have been linked in the proper sequence, any remaining protecting groups are removed sequentially or concurrently, and the peptide chain, if synthesized by the solid phase method, is cleaved from the solid support to afford the final polypeptide. By simple modification of this general produced, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing peptides involves solid phase peptide synthesis. In this method of preparing peptides, the alpha-amino function of the amino acids is protected by an acid or base sensitive group. Such protecting groups should have the properties of being stable to the conditions of peptide linkage formation, while being readily removable without destruction of the growing peptide chain or racemization of any of the chiral centers container therein. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha,alpha)-dimethyl-3,5dimethoxybenzyloxycarbonyl, o-nitrophenylsulfenyl, 2-cyano-t-butyloxycarbonyl, 9-fluorenylmethyloxycarbonyl (FMOC) and the like. The t-butyloxycarbonyl ("BOC" or "t-BOC")protecting group is preferred.

Particularly preferred side chain protecting groups are, for side-chain amino groups as in lysine and arginine: nitro, p-toluene-sulfonyl, 4-methoxybenzenesulfonyl, Cbz, BOC, FMOC and adamantyloxycarbonyl; for tyrosine: benzyl, o-bromo-benzyloxycarbonyl, 2,6-dichlorobenzyl, isopropyl, cyclohexyl, cyclopentyl and acetyl; for serine: benzyl and tetrahydropyranyl; for histidine: benzyl, Cbz, p-toluenesulfonyl and 2,4-dinitrophenyl; for tryptophan: formyl; for side-chain carboxylic groups as in Glu or Asp: benzyl or FMOC.

In the solid phase peptide synthesis method, the C-terminal amino acid is attached to a suitable solid support. Suitable solid supports useful for the above synthesis are those materials which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. Chloromethyl-polystyrene-1% divinylbenzene polymer is especially preferred. For the special case where the C-terminus of the compound is glycinamide, a particularly useful support is the benzhydrylamino-polystyrene-divinylbenzene polymer described by P. Rivaille, et al, Helv. Chim. Acta, 54, 2772(1971). The coupling to the chloromethyl polystyrene-divinylbenzene type of resin is made by means of the reaction of the alpha-N-protected amino acid, especially the BOC-amino acid, as its cesium, tetramethylammonium, triethylammonium, 1,5-diazabicyclo-[5.4.0]undec-5-ene, or similar salt. The coupling reaction is accomplished in a solvent such as ethanol, acetonitrile, N,N-dimethylformamide (DMF), and the like, with the chloromethyl resin at an elevated temperature, for example between about 40° and 60° C., for from about 12 to 48 hours. Preferred reagents and reaction conditions involve the coupling of an alpha-N-BOC amino acid cesium salt with the resin in DMF at about 50° C. for about 24 hours. The alpha-N-BOC-amino acid is attached to the benzhydrylamine resin by means of N,N'-dicyclohexylcarbodiimide (DCC) or N,N'-diisopropylcarbodiimide (DIC) with or without 1-hydroxybenzotriazole (HOBt), benzotriazol-1-yloxy-tris(dimethylamino)phosphonium-hexafluorophosphate (BOP) or bis(2-oxo-3-oxazolidinyl)phosphine chloride (BOPCl), mediated coupling for from about 1 to about 24 hours, preferably about 12 hours at a temperature of between about 10° to 50° C., most preferably 25° C. in a solvent such as dichloromethane or DMF, preferably dichloromethane.

The coupling of successive protected amino acids can be carried out in an automatic polypeptide synthesizer as is well known in the art. The removal of the alpha-N-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in 0.4M concentration and approximately 3.5 molar excess and the coupling may be carried out in dichloromethane, dichloromethane/DMF mixtures, DMF and the like, especially in methylene chloride at about ambient temperature. The coupling agent is normally DCC in diochloromethane but may be N,N'-di-isopropylcarbodiimide (DIC) or other carbodiimide either alone or in the presence of HOBt, N-hydroxysuccinimide, other N-hydroxyimides or oximes. Alternately, protected amino acid active ester (e.g. p-nitrophenyl, pentafluorophenyl and the like) or symmetrical anhydrides may be used.

GENERAL PROCEDURE FOR PEPTIDE CYCLIZATION

The cyclization of the resulting peptide is accomplished either by a solution cyclization of the deprotected peptide after HF cleavage from the resin, or on the resin bound peptide prior to HF treatment.

When the peptide is to be cyclized in solution, suitable protecting groups are selected so that upon HF cleavage a free carboxylate and a free amine are exposed at the points where cyclization is desired. After synthesis, cleavage from the resin, and deprotection, the peptide is cyclized by slowly adding a solution of the peptide to a slightly basic solution of diphenylphosphoryl azide in DMF at 0° C. Upon completion of the cyclization (by RP-HPLC analysis) the reaction is quenched with water, concentrated, and the peptide purified by preparative reverse phase high pressure liquid phase chromatography (RP-HPLC).

When the peptide is to be cyclized bound to the resin, the FMOC protecting group is utilized on the side chains between which cyclization is to be accomplished. Upon completion of the synthesis the peptide-resin is suspended in a 40% piperidine/DMF mixture for 60 min to remove the FMOC group. The peptide-resin is then washed with DMF, and the peptide cyclized by suspending the peptide-resin in DMF containing 1% diisopropylethylamine (DIEA) and treating the suspension with BOP [benzotriazolyl-N-oxytris-(dimethylamino)-phosphonium hexafluorophosphate] reagent (3 equiv.) at ambient temperature for 12–48 hr. The peptide-resin is then washed successively with $CH_2Cl_2$, MeOH, $CH_2Cl_2$, and dried overnight over $P_2O_5$ under vacuum prior to cleavage and global deprotection with HF. Preparative RP-HPLC is then utilized to purify the cyclic peptide.

LHRH ANTAGONIST ACTIVITY

Representative compounds of the present invention were evaluated in an in vitro test for LHRH antagonist potency ($pA_2$). The test employed the method detailed in F. Haviv, et al. J. Med. Chem., 32: 2340–2344 (1989). The values of $pA_2$ are the negative logarithms of the concentration of the particular antagonist test compound required to shift the response curve produced by the agonist leuprolide to two-fold higher concentration. (Leuprolide is the LHRH agonist having the structure 5-oxo-Pro $^1$-His$^2$-Trp$^3$-Ser$^4$-Tyr$^5$-D-Leu$^6$-Leu$^7$-Arg$^8$-Pro-$^9$-NHEt and is disclosed and claimed in U.S. Pat. No. 4,005,063.) Typically $pA_2$ values of 6.0 or greater are indicative of acceptable LHRH antagonist potency, with compounds having $pA_2$ values of 9.0 or greater being preferred.

The results of those tests for representative compounds of the present invention are given in the following table.

| Example | $pA_2$ |
| --- | --- |
| 1 | 10.16 |
| 2 | 9.27 |
| 3 | 8.73 |
| 4 | 10.05 |
| 5 | 8.2 |
| 6 | 7.54 |
| 7 | 9.58 |
| 8 | 9.66 |
| 9 | 8.21 |
| 10 | 6.14 |
| 11 | 7.69 |
| 12 | 9.77 |

| Example | pA$_2$ |
| --- | --- |
| 13 | 7.72 |
| 14 | 9.52 |
| 15 | 5.66 |
| 16 | 7.39 |
| 17 | 8.29 |
| 18 | <6.0 |
| 19 | 5.95 |

The compounds of the present invention act as LHRH antagonists and are useful for suppressing levels of gonadotropins and androgens in mammals in the treatment of prostate cancer, endometriosis, uterine fibroids, precocious puberty, and other sex hormone dependent disease conditions.

In the practice of the method of this invention an amount of a compound of the invention or a pharmaceutical composition containing the antagonists, effective to (including subcutaneous, intramuscular and intraveneous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to mediate levels of sex hormones in male or female mammals for the uses hereinabove described, it is expedient to administer the active ingredients in amounts between about 0.01 and 10 mg/kg of body weight per day, preferably between about 0.1 to 5.0 mg/kg of body weight per day. This administration may be accompliahed by a single daily administration, by administration over several applications or by slow release in order to achieve the most effective results.

The exact doe and regiment for administration of these compounds and compositions will necessarily be dependent upon the needs of the individual subject being treated, the type of treatment, the degree of affliction or need and the judgment of the medical practitioner. In general, parenteral administration requires lower dosage than other methods of administration which are more dependent upon absorption. However, it is within the skill of the medical arts to "titrate" the subject; i.e. to begin by administering a lower dose of the compounds that is required to achieve the desired effect and gradually increasing the dose until the desired effect is achieved.

A further aspect of the present invention relates to pharmaceutical compositions containing as active ingredienmt a compound of the present invention which compositions comprise such a compound in admixture with a pharmaceutically acceptable, non-toxic carrier. As mentioned above, such compositions may be prepared for use for parenteral (subcutaneous, intramuscular or intraveneous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono-or di-sulfonic acids, polygalacturonic acid, and the like; (b) a salt with a polyvalent metal cation such as zinc, calcium bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Druq Delivery Systems, J. R. Robinson ed., Marcel Dekker, Inc., New York, 1978. Particular reference with respect to LHRH type compounds may be found, for example, in U.S. Pat. No. 4,010,125.

The following examples are given as representative compounds of the present invention. These examples are merely illustrative of the invention and are not to be read as limiting the scope of the invention as it is described by the appended claims.

EXAMPLE 1

Ac-D2Nal-D4ClPhe-c-{DLys-Ser-NMeTyr-DLys-(Nicotinyl)-Leu-Lys(N-epsilon-Isopropyl)-Pro-DGlu}-NH$_2$ In the reaction vessel of a Milligen-Biosearch 9500 peptide synthesizer was placed 2 g (0.65 mmol) of MBHA (4-methyl-benzhydrylamine) resin. N-Boc-D-Glutamic acid-γ-Benzyl ester was coupled to the resin utilizing the Base Wash, Coupling, Wash portion of the following synthetic cycle. Subsequent amino acids were added sequentially utilizing the complete synthetic cycle:

1. Deblocking to remove the t-BOC group from the alpha-amino function of the peptide, is carried out using a solution of 45% trifluoroacetic acid (TFA), 2.5% anisole, 2.0% dimethyl phosphite, and 50.5% methylene chloride. The resin is prewashed with the deblocking solution for one minute and then the deblocking reaction is run for 20 minutes.
2. Base wash, to remove and neutralize the TFA used for deprotection, is carried out using a solution of 10% N,N'-diisopropylethylamine in methylene chloride. The resin is washed with base three times for one minute each time after a deblocking step.
3. Coupling reaction is carried out using a 4-fold molar excess of 0.3M DMF solution of a t-BOC protected amino acid derivative along with a 3-fold molar excess of 0.3M methylene chloride solution of diisopropylcarbodiimide as activator. The activated amino acid is then coupled to the free alpha amino group of the peptide-resin. The reaction time is as described in the synthesis protocol.
4. Wash, each reaction step is followed by three washes of one minute each: one of methylene chloride, one of (1:1) methylene chloride/DMF, and one of DMF.

Synthesis Protocol

The amino protected amino acids are coupled to the resin according the following order, number, and duration of couplings:

| # | Amino Acid | Coupling |
|---|---|---|
| 1. | Boc-D-Glu(OBz) | two-3h |
| 2. | BOC-Pro | two-2h |
| 3. | BOC-Lys(N-epsilon-Cbz,Isopropyl) | two-2h |
| 4. | BOC-Leu | two-2h |
| 5. | BOC-D-Lys(N-epsilon-Nicotinyl) | two-2h |
| 6. | BOC-NMe-Tyr(O-2,6-diCl-Bzl) | two-2h |
| 7. | BOC-Ser(OBzl) | two-2h |
| 8. | BOC-D-Lys(N-epsilon-Cbz) | two-2h |
| 9. | BOC-D-4ClPhe | two-2h |
| 10. | BOC-D2Nal | two-2h |
| 11. | acetic acid | two-2h |

Upon completion of the synthesis the resin is dried overnight over $P_2O_5$ under vacuum and then 1 g of dried resin is treated with dry HF in the presence of anisole at 0° C. for 1 h to cleave the peptide from the resin. The excess reagent is removed in vacuo. The resin is washed first with ether, then stirred at room temperature with a solution of (1:1) water/acetonitrile (50 ml) for 15 minutes, and filtered. The filtrate is lyophilized to give the crude peptide as a fluffy powder. The crude peptide (797 mg, 0.51 mmol) is dissolved in 10 ml of anhydrous DMF and added dropwise via syringe pump over a 6.4 h period to a cold (0° C.) mixture of DMF (100 mL), Diisopropylethylamine (2.5 mmol), and Diphenylphosphoryl azide (2.5 mmol). Upon completion of the addition, the mixture is allowed to warm to ambient temperature and is stirred under $N_2$ atmosphere for 24 h. At this time RP-HPLC analysis of the reaction mixture indicates complete consumption of starting material. The reaction mixture is quenched with 1 mL of 0.1% aq. trifluoroacetic acid solution and concentrated. The crude reaction mixture is purified by HPLC using a (25×2.5 cm) Dynamax C-18 column (8 micron) with solvent mixtures varying in a gradient ranging from 75% $H_2O$/25% $CH_3CN$/0.1% TFA to 30% $H_2O$/70% $CH_3CN$/0.1% TFA over a period of 45 minutes. The UV detector is set at 254 nM. The product is eluted as a single peak, collected and lyophilized to give pure Ac-D2Nal-D4ClPhe-c-{DLys-Ser-NMeTyr-DLys(Nicotinyl)-Leu-Lys(N-epsilon-Isopropyl)-Pro-DGlu}-NH$_2$ as the trifluoroacetate salt. Rt=20.40 min. FAB Mass spec. m/e 1554 (M+H)$^+$. Amino Acid Anal: 1.01 Glu; 1.02 Pro; 0.97 (Lys(Isp)); 1.03 Leu; 1.95 Lys; 1.11 NMeTyr; 0.53 Ser; 1.12 4ClPhe.

EXAMPLE 2

Ac-D2Nal-D4ClPhe-c-{DLys-Ser-Tyr-DLys-(Nicotinyl)-Leu-Lys(N-epsilon-Isopropyl)-Pro-Glu}-NH$_2$ In the reaction vessel of a Milligen-Biosearch 9500 peptide synthesizer was placed 1.5 g (0.34 mmol) of MBHA (4-methyl-benzhydrylamine) resin. N-Boc-D-Glutamic acid-g-Fluorenylmethyl ester was coupled to the resin utilizing the Base Wash, Coupling, Wash portion of the following synthetic cycle. Subsequent amino acids were added sequentially utilizing the complete synthetic cycle:

1. Deblocking to remove the t-BOC group from the alpha-amino function of the peptide, is carried out using a solution of 45% trifluoroacetic acid (TFA), 2.5% anisole, 2.0% dimethyl phosphite, and 50.5% methylene chloride. The resin is prewashed with the deblocking solution for one minute and then the deblocking reaction is run for 20 minutes.
2. Base wash, to remove and neutralize the TFA used for deprotection, is carried out using a solution of 10% N,N'-diisopropylethylamine in methylene chloride. The resin is washed with base three times for one minute each time after a deblocking step.
3. Coupling reaction is carried out using a 3-fold molar excess of 0.3M DMF solution of a t-BOC protected amino acid derivative along with a 3-fold molar excess of 0.3M methylene chloride solution of diisopropylcarbodiimide as activator. The activated amino acid is then coupled to the free alpha amino group of the peptide-resin. The reaction time is as described in the synthesis protocol.
4. Wash, each reaction step is followed by three washes of one minute each: one of methylene chloride, one of (1:1) methylene chloride/DMF, and one of DMF.

Synthesis Protocol

The amino protected amino acids are coupled to the resin according the following order, number, and duration of couplings:

| # | Amino Acid | Coupling |
|---|---|---|
| 1. | Boc-D-Glu(OFmoc) | two-6h |
| 2. | BOC-Pro | two-2h |
| 3. | BOC-Lys(N-epsilon-Cbz,Isopropyl) | two-2h |
| 4. | BOC-Leu | two-2h |
| 5. | BOC-D-Lys(N-epsilon-Nicotinyl) | two-2h |
| 6. | BOC-Tyr(O-2Br-Cbz) | two-2h |
| 7. | BOC-Ser(OBzl) | two-2h |
| 8. | BOC-D-3Pal | two-2h |
| 9. | BOC-D-4ClPhe | two-2h |
| 10. | BOC-D2Nal | two-2h |
| 11. | acetic acid | two-2h |

Upon completion of the synthesis the DLys and Glu residues of the peptide-resin were selectively deprotected by treatment with 40 mL of a 40% piperidine/DMF mixture for 60 min. The peptide-resin was then washed with DMF, and the peptide cyclized by suspending the peptide-resin in DMF (50 mL) containing 1% DIEA and treating with BOP [Benzotriazolyl-N-oxytris(dimethylamino)phosphonium hexafluorophosphate] reagent (3 equiv.) at ambient temperature overnight. The peptide-resin was then washed with $CH_2Cl_2$, MeOH, $CH_2Cl_2$, and dried overnight over $P_2O_5$ under vacuum prior to treatment with dry HF in the presence of anisole at 0° C. for 1 h to cleave the peptide from the resin. The excess reagent is removed in vacuo. The resin is washed first with ether, then stirred at room temperature with a solution of (1:1) water/acetonitrile (50 ml) for 15 minutes, and filtered. The filtrate is lyophilized to give the crude peptide as a fluffy powder. The crude reaction mixture is purified by HPLC using a (25×2.5 cm) Dynamax C-18 column (8 micron) with solvent mixtures varying in a gradient ranging from 75% $H_2O$/25% $CH_3CN$/0.1% TFA to 30% $H_2O$/70% $CH_3CN$/0.1% TFA over a period of 45 minutes. The UV detector is set at 254 nM. The product is eluted as a single peak, collected and lyophilized to give pure Ac-D2Nal-D4ClPhe-c-{ DLys-Ser-Tyr-DLys(Nicotinyl)-Leu-Lys(N-epsilon-Isopropyl)-Pro-Glu}-$NH_2$ as the trifluoroacetate salt. Rt=14.2 min. FAB Mass spec. m/e 1540 $(M+H)^+$. Amino Acid Anal: 0.97 Glu; 1.03 Pro; 0.89 (Lys(Isp)); 1.02 Leu; 1.98 Lys; 0.93 Try; 0.52 Ser; 1.06 4ClPhe.

EXAMPLE 3

Ac-D2Nal-D4ClPhe-c-{Lys-Ser-NMeTyr-DLys(Nicotinyl)-Leu-Lys(N-epsilon-Isopropyl)-Pro-DGlu}-$NH_2$ The procedure described in Example 1 was used, but substituting BOC-Lys(N-epsilon-Cbz) for BOC-DLys(N-epsilon-Cbz). After work-up and HPLC purification Ac-D2Nal-D4ClPhe-c-{Lys-Ser-NMeTyr-DLys(Nicotinyl)-Leu-Lys(N-epsilon-Isopropyl)-Pro-DGlu}-$NH_2$ was obtained as trifluoroacetate salt; Rt=20.6 min; FAB Mass spec m/e 1554 (M+H)+; Amino Acid Anal: 0.99 Glu; 0.95 Pro; 0.95 Lys(Isp); 1.04 Leu; 2.01 Lys; 1.09 NMeTyr; 0.41 Ser; 1.1 4ClPhe.

EXAMPLE 4

Ac-D2Nal-D4ClPhe-c-{DLys-Ser-NMeTyr-DLys(Nicotinyl)-Leu-Lys(N-epsilon-Isopropyl)-Pro-Glu}-$NH_2$ The procedure described in Example 1 was used, but substituting BOC-Glu(OBzl) for BOC-DGlu(OBzl). After work-up and HPLC purification Ac-D2Nal-D4ClPhe-c-{DLys-Ser-NMeTyr-DLys(Nicotinyl)-Leu-Lys(N-epsilon-Isopropyl)-Pro-Glu}-$NH_2$ was obtained as trifluoroacetate salt; Rt=20.9 min; FAB Mass spec m/e 1554 (M+H)+; Amino Acid Anal: 1.04 Glu; 0.94 Pro; 0.97 Lys(Isp); 0.99 Leu; 2.04 Lys; 1.73 NMeTyr; 0.50 Ser; 1.07 4ClPhe.

EXAMPLE 5

Ac-D2Nal-D4ClPhe-c-{Lys-Ser-NMeTyr-DLys(Nicotinyl)-Leu-Lys(N-epsilon-Isopropyl)-Pro-Glu}-$NH_2$ The procedure described in Example 1 was used, but substituting BOC-Lys(N-epsilon-Cbz) and BOC-Glu(OBzl) for BOC-DLys(N-epsilon-Cbz) and BOC-DGlu(OBzl), respectively. After work-up and HPLC purification Ac-D2Nal-D4ClPhe-c-{Lys-Ser-NMeTyr-DLys(Nicotinyl)-Leu-Lys(N-epsilon-Isopropyl)-Pro-Glu}-$NH_2$ was obtained as trifluoroacetate salt; Rt=20.3 min; FAB Mass spec m/e 1554 (M+H+; Amino Acid Anal: 0.97 Glu; 1.00 Pro; 0.98 Lys(Isp); 0.99 Leu; 2.05 Lys; 1.33 NMeTyr; 0.502 Ser; 1.05 4ClPhe.

EXAMPLE 6

Ac-D2Nal-D4ClPhe-c-{Glu-Ser-NMeTyr-DLys(Nicotinyl)-Leu-Lys(N-epsilon-Isopropyl)-Pro-DOrn}-$NH_2$ The procedure described in Example 1 was used, but substituting BOC-Glu(OBzl) and BOC-DOrn(N-d-Cbz) for BOC-DLys(N-epsilon-Cbz) and BOC-DGlu(OBzl), respectively. After work-up and HPLC purification Ac-D2Nal-D4ClPhe-c-{Glu-Ser-NMeTyr-DLys(Nicotinyl)-Leu-Lys(N-epsilon-Isopropyl)-Pro-DOrn}-$NH_2$ was obtained as trifluoroacetate salt; Rt=19.0 min; FAB Mass spec m/e 1540 (M+H)+; Amino Acid Anal: 0.97 Orn, 0.95 Pro; 0.87 Lys(Isp); 1.05 Leu; 1.01 Lys; 1.33 NMeTyr; 0.82 Ser; 0.99 Glu; 0.99 4ClPhe.

EXAMPLE 7

Ac-D2Nal-D4ClPhe-c-{DGlu-Ser-NMeTyr-DLys(Nicotinyl)-Leu-Lys(N-epsilon-Isopropyl)-Pro-DLys}-$NH_2$ The procedure described in Example 1 was used, but substituting BOC-DGlu(O-bzl) for BOC-DLys(N-epsilon-Cbz) and BOC-DLys(N-epsilon-Cbz) for BOC-DGlu(O-Bzl). After work-up and HPLC purification Ac-D2Nal-D4ClPhe-c-{DGlu-Ser-NMeTyr-DLys(Nicotinyl)-Leu-Lys(N-epsilon-Isopropyl)-Pro-DLys}-$NH_2$ was obtained as trifluoroacetate salt; Rt=31.2 min; FAB Mass spec m/e 1554 (M+H)+; Amino Acid Anal: 1.96 Lys; 1.05 Pro; 0.92 Lys(Isp); 1.01 Leu; 1.13 NMeTyr; 0.43 Ser; 0.98 Glu; 1.13 4ClPhe.

EXAMPLE 8

Ac-D2Nal-D4ClPhe-c-{DLys-Ser-Tyr-DLys-(Nicotinyl)-Leu-Lys(N-epsilon-Isopropyl)-Pro-DGlu}-$NH_2$ The procedure described in Example 1 was used, but substituting BOC-Tyr(O-2Br-Cbz) for BOC-NMeTyr(O-2,6-diCl-Bzl). After work-up and HPLC purification Ac-D2Nal-D4ClPhe-c-{DLys-Ser-Tyr-DLys(Nicotinyl)-Leu-Lys(N-epsilon-Isopropyl)-Pro-DGlu}-$NH_2$ was obtained as trifluoroacetate salt; Rt=29.9 min; FAB Mass spec m/e 1540 (M+H)+; Amino Acid Anal: 0.96 Glu; 1.01 Pro; 0.81 Lys(Isp); 1.01 Leu; 2.05 Lys; 0.97 Tyr; 0.58 Ser; 1.17 4ClPhe.

EXAMPLE 9

Ac-c-{DLys-Ser-NMeTyr-DLys(Nicotinyl)-Leu-Lys(N-epsilon-Isopropyl)-Pro-DGlu}-$NH_2$ The procedure described in Example 1 was used, but deleting the BOC-D4ClPhe and BOC-D2Nal from the protocol. After work-up and HPLC purification Ac-c-{DLys-Ser-NMeTyr-DLys(Nicotinyl)-Leu-Lys(N-epsilon-Isopropyl)-Pro-DGlu}-$NH_2$ was obtained as trifluoroacetate salt; Rt=26.8 min; FAB Mass spec m/e 1176 (M+H)+; Amino Acid Anal: 0.98 Glu; 0.99 Pro; 0.90 Lys(Isp); 1.01 Leu; 2.02 Lys; 1.09 NMeTyr; 0.42 Ser.

EXAMPLE 10

4F-Phenylacetyl-c-{DLys-Ser-NMeTyr-DLys(Nicotinyl)-Leu-Lys(N-epsilon-Isopropyl)-Pro-DGlu}-NH$_2$ The procedure described in Example 9 was used, but substituting 4-FPhenylacetic acid for acetic acid. After work-up and HPLC purification 4FPhenylacetyl-c-{ DLys-Ser-NMeTyr-DLys(Nicotinyl)-Leu-Lys(N-epsilon-Isopropyl)-Pro-DGlu}-NH$_2$ was obtained as trifluoroacetate salt; Rt=29.9 min; FAB Mass spec m/e 1270 (M+H)+; Amino Acid Anal: 0.95 Glu; 1.01 Pro; 0.64 Lys(Isp); 1.00 Leu; 2.04 Lys; 0.86 NMeTyr; 0.40 Ser.

EXAMPLE 11

Ac-c-{DGlu-Ser-NMeTyr-DLys(Nicotinyl)-Leu-Lys(N-epsilon-Isopropyl)-Pro-DLys}-NH$_2$ The procedure described in Example 9 was used, but substituting BOC-DGlu(OBzl) for BOC-DLys(N-epsilon-Cbz) and BOC-DLys(N-epsilon-Cbz) for BOC-DGlu(OBzl). After work-up and HPLC purification Ac-c-{DGlu-Ser-NMeTyr-DLys(Nicotinyl)-Leu-Lys(N-epsilon-Isopropyl)-Pro-DLys}-NH$_2$ was obtained as trifluoroacetate salt; Rt=24.9 min; FAB Mass spec m/e 1176 (M+H)+; Amino Acid Anal: 2.03 Lys; 1.02 Pro; 1.24 Lys(Isp); 1.06 Leu; 1.02 NMeTyr; 0.35 Ser; 0.95 Glu.

EXAMPLE 12

Ac-D2Nal-D4ClPhe-c-{DGlu-Ser-NMeTyr-DLys(Nicotinyl)-Leu-Lys(N-epsilon-Isopropyl)-Pro-Lys}-NH$_2$ The procedure described in Example 1 was used, but substituting BOC-DGlu(OBzl) for BOC-DLys(N-epsilon-Cbz) and BOC-Lys(N-epsilon-Cbz) for BOC-DGlu(OBzl). After work-up and HPLC purification Ac-D2Nal-D4ClPhe-c-{DGlu-Ser-NMeTyr-DLys(Nicotinyl)-Leu-Lys(N-epsilon-Isopropyl)-Pro-Lys}-NH$_2$ was obtained as trifluoroacetate salt; Rt=20.3 min; FAB Mass spec m/e 1554 (M+H)+; Amino Acid Anal: 2.04 Lys; 1.00 Pro; 1.26 Lys(Isp); 1.00 Leu; 1.07 NMeTyr; 0.45 Ser; 0.95 Glu; 1.12 4ClPhe.

EXAMPLE 13

4ClPhenylpropionyl-c-{DLys-Ser-NMeTyr-DLys(Nicotinyl)-Leu-Lys(N-epsilon-Isopropyl)-Pro-DGlu}-NH$_2$ The procedure described in Example 10 was used, but substituting 4-Clphenylpropionic acid for 4-Fphenylacetic acid. After work-up and HPLC purification 4ClPhenylpropionyl-c-{DLys-Ser-NMeTyr-DLys(Nicotinyl)-Leu-Lys(N-epsilon-Isopropyl)-Pro-DGlu}-NH$_2$ was obtained as trifluoroacetate salt; Rt=23.4 min; FAB Mass spec m/e 1300 M+H)+; Amino Acid Anal: 0.96 Glu; 1.01 Pro; 1.30 Lys(Isp); 1.01 Leu; 2.02 Lys; 1.08 NMeTyr; 0.46 Ser.

EXAMPLE 14

Ac-D2Nal-D4ClPhe-c-{DOrn-Ser-NMeTyr-DLys(Nicotinyl)-Leu-Lys(N-epsilon-Isopropyl)-Pro-DGlu}-NH$_2$ The procedure described in Example 1 was used, but substituting BOC-DOrn(Cbz) for BOC-DLys(Cbz). After work-up and HPLC purification Ac-D2Nal-D 4ClPhe-c-{DOrns-Ser-NMeTyr-DLys(Nicotinyl)-Leu-Lys(N-epsilon-Isopropyl)-Pro-DGlu}-NH$_2$ was obtained as trifluoroacetate salt; Rt=20.5 min; FAB Mass spec m/e 1540 (M+H)+; Amino Acid Anal: 1.08 Glu; 1.07 Pro; 1.28 Lys(Isp); 0.93 Leu; 0.92 Lys; 0.96 NMeTyr; 0.79 Ser; 1.00 Orn; 0.72 4ClPhe.

EXAMPLE 15

4FPhenylacetyl-c-{DGlu-Ser-NMeTyr-DLys-(Nicotinyl)-Leu-Lys(N-epsilon-Isopropyl)-Pro-DLys}-NH$_2$ The procedure described in Example 7 was used, but substituting 4-fluorophenylpropionic acid for BOC-D4ClPhe and skipping the coupling with BOC-D2Nal and acetic acid. After work-up and HPLC purification 4F-propionyl-c-{DGlu-Ser-NMeTyr-DLys(Nicotinyl)-Leu-Lys(N-epsilon-Isopropyl)-Pro-DLys}-NH$_2$ was obtained as trifluoroacetate salt; Rt=30.1 min; FAB Mass spec m/e 1270 (M+H)+; Amino Acid Anal: 2.02 Lys; 1.01 Pro; 1.17 Lys(Isp); 1.01 Leu; 2.02 Lys; 1.40 NMeTyr; 0.46 Ser; 0.97 Glu.

EXAMPLE 16

4ClPhenylpropionyl-c-{DLys-Ser-NMeTyr-DLys(Nicotinyl)-Leu-Lys(N-epsilon-Isopropyl)-Gly-DGlu}-NH$_2$ The procedure described in Example 13 was used, but substituting BOC-Gly for BOC-Pro. After work-up and HPLC purification 4ClPhenylpropionyl-c-{ DLys-Ser-NMeTyr-DLys(Nicotinyl)-Leu-Lys(N-epsilon-Isopropyl)-Gly-DGlu}-NH$_2$ was obtained as trifluoroacetate salt; Rt=21.4 min; FAB Mass spec m/e 1260 (M+H)+; Amino Acid Anal: 0.97 Glu; 1.01 Gly; 1.16 Lys(Isp); 0.99 Leu; 2.02 Lys; 1.10 NMeTyr; 0.47 Ser.

EXAMPLE 17

NAc-D2Nal D4ClPhe-c-{DLys-Gly-NMeTyr-DLys(Nicotinyl)-Leu-Lys(N-epsilon-Isopropyl)-Gly-DGlu}-NH$_2$ The procedure described in Example 1 was used, but substituting BOC-Gly for BOC-Ser(OBzl) and for BOC-Pro. After work-up and HPLC purification NAc-D2Nal-D4ClPhe-c-{DLys-Gly-NMeTyr-DLys(Nicotinyl)-Leu-Lys(N-epsilon-Isopropyl)-Gly-DGlu}-NH$_2$ was obtained as trifluoroacetate salt; Rt=19.1 min; FAB Mass spec m/e 1484 (M+H)+; Amino Acid Anal: 0.97 Glu; 1.97 Gly; 0.60 Lys(Isp); 1.00 Leu; 2.03 Lys; 1.12 NMeTyr.

EXAMPLE 18

4ClPhepropionyl-c-{DLys-Gly-NMeTyr-DLys-(Nicotinyl)-Leu-Lys(N-epsilon-Isopropyl)-Gly-DGlu}-NH₂

The procedure described in Example 17 was used, but substituting 4ClPhenylpropionic acid for BOC-4ClDPhe and skipping the coupling with BOC-D2Nal and acetic acid. After work-up and HPLC purification 4ClPhepropionyl-c-{DLys-Gly-NMeTyr-DLys(Nicotinyl)-Leu-Lys(N-epsilon-Isopropyl)-Gly-DGlu}-NH₂ was obtained as trifluoroacetate salt; Rt=22.1 min; FAB Mass spec m/e 1230 (M+H)+; Amino Acid Anal: 0.94 Glu; 1.97 Gly; 0.62 Lys(Isp); 1.01 Leu; 2.07 Lys; 1.17 NMeTyr.

EXAMPLE 19

NAc-c-{DGlu-Gly-NMeTyr-DLys(Nicotinyl)-Leu-Lys(N-epsilon-Isopropyl)-Sar-DLys}-NH₂

The procedure described in Example 11 was used, but substituting BOC-Sar for BOC-Pro. After work-up and HPLC purification NAc-c-{DGlu-Gly-NMeTyr-DLys(Nicotinyl)-Leu-Lys(N-epsilon-Isopropyl)-Sar-DLys}-NH₂ was obtained as trifluoroacetate salt; Rt=22.9 min; FAB Mass spec m/e 1149 (M+H)+; Amino Acid Anal: 2.04 Lys; 1.26 Lys(Isp); 1.00 Leu; 2.04 Lys; 0.99 NMeTyr; 0.28 Ser.

EXAMPLE 20

Using the procedure described in Example 1, but substituting the appropriate Boc-amino acids instead of Boc-DLys(N-epsilon-Cbz) and Boc-DGlu(OBz) the following compounds are obtained:

Ac-D2Nal-D4ClPhe-c-{DHLys-Ser-NMeTyr-DLys(Nicotinyl)-Leu-Lys(N-epsilon-Isopropyl)-Pro-DAsp}-NH₂
Ac-D2Nal-D4ClPhe-c-{DHLys-Ser-NMeTyr-DLys(Nicotinyl)-Leu-Lys(N-epsilon-Isopropyl)-Pro-DGlu}-NH₂
Ac-D2Nal-D4ClPhe-c-{DHLys-Ser-NMeTyr-DLys(Nicotinyl)-Leu-Lys(N-epsilon-Isopropyl)-Pro-DHGlu}-NH₂
Ac-D2Nal-D4ClPhe-c-{DDap-Ser-NMeTyr-DLys(Nicotinyl)-Leu-Lys(N-epsilon-Isopropyl)-Pro-DAsp}-NH₂
Ac-D2Nal-D4ClPhe-c-{DDap-Ser-NMeTyr-DLys(Nicotinyl)-Leu-Lys(N-epsilon-Isopropyl)-Pro-DGlu}-NH₂
Ac-D2Nal-D4ClPhe-c-{DDap-Ser-NMeTyr-DLys(Nicotinyl)-Leu-Lys(N-epsilon-Isopropyl)-Pro-DHGlu}-NH₂
Ac-D2Nal-D4ClPhe-c-{DLys-Ser-NMeTyr-DLys(Nicotinyl)-Leu-Lys(N-epsilon-Isopropyl)-Pro-DAsp}-NH₂
Ac-D2Nal-D4ClPhe-c-{DLys-Ser-NMeTyr-DLys(Nicotinyl)-Leu-Lys(N-epsilon-Isopropyl)-Pro-DHGlu}-NH₂
Ac-D2Nal-D4ClPhe-c-{DOrn-Ser-NMeTyr-DLys(Nicotinyl)-Leu-Lys(N-epsilon-Isopropyl)-Pro-DAsp}-NH₂
Ac-D2Nal-D4ClPhe-c-{DOrn-Ser-NMeTyr-DLys(Nicotinyl)-Leu-Lys(N-epsilon-Isopropyl)-Pro-DHGlu}-NH₂ and
Ac-D2Nal-D4ClPhe-c-{DGlu-Ser-NMeTyr-DLys(Nicotinyl)-Leu-Lys(N-epsilon-Isopropyl)-Pro-DOrn}-NH₂.

EXAMPLE 21

Using the procedure described in Example 20, but interchanging the Box-amino acids at positions 3 and 10, the following compounds are obtained.

Ac-D2Nal-D4ClPhe-c-{DGlu-Ser-NMeTyr-DLys(Nicotinyl)-Leu-Lys(N-epsilon-Isopropyl)-Pro-DHLys}-NH₂
Ac-D2Nal-D4ClPhe-c-{DHGlu-Ser-NMeTyr-DLys(Nicotinyl)-Leu-Lys(N-epsilon-Isopropyl)-Pro-DHLys}-NH₂
Ac-D2Nal-D4ClPhe-c-{DAsp-Ser-NMeTyr-DLys(Nicotinyl)-Leu-Lys(N-epsilon-Isopropyl)-Pro-DHLys}-NH₂
Ac-D2Nal-D4ClPhe-c-{DGlu-Ser-NMeTyr-DLys(Nicotinyl)-Leu-Lys(N-epsilon-Isopropyl)-Pro-DDap}-NH₂
Ac-D2Nal-D4ClPhe-c-{DHGlu-Ser-NMeTyr-DLys(Nicotinyl)-Leu-Lys(N-epsilon-Isopropyl)-Pro-DDap}-NH₂
Ac-D2Nal-D4ClPhe-c-{DAsp-Ser-NMeTyr-DLys(Nicotinyl)-Leu-Lys(N-epsilon-Isopropyl)-Pro-DDap}-NH₂
Ac-D2Nal-D4ClPhe-c-{DHGlu-Ser-NMeTyr-DLys(Nicotinyl)-Leu-Lys(N-epsilon-Isopropyl)-Pro-DOrn}-NH₂
Ac-D2Nal-D4ClPhe-c-{DAsp-Ser-NMeTyr-DLys(Nicotinyl)-Leu-Lys(N-epsilon-Isopropyl)-Pro-DOrn}-NH₂
Ac-D2Nal-D4ClPhe-c-{DHGlu-Ser-NMeTyr-DLys(Nicotinyl)-Leu-Lys(N-epsilon-Isopropyl)-Pro-DLys}-NH₂ and
Ac-D2Nal-D4ClPhe-c-{DAsp-Ser-NMeTyr-DLys(Nicotinyl)-Leu-Lys(N-epsilon-Isopropyl)-Pro-DLys}-NH₂.

EXAMPLE 22

Using the procedure described in Example 1, but substituting the appropriate Boc-amino acid instead of Boc-D2Nal, the following compounds are obtained:

Ac-D3Qal-D4ClPhe-c-{DLys-Ser-NMeTyr-DLys(Nicotinyl)-Leu-Lys(N-epsilon-Isopropyl-Pro-DGlu}-NH₂
Ac-D4ClPhe-D4-1 ClPhe-c-{DLys-Ser-NMeTyr-DLys(Nicotinyl)-Leu-Lys(N-epsilon-Isopropyl)-Pro-DGlu}-NH₂
Ac-DPhe-D4ClPhe-c-{DLys-Ser-NMeTyr-DLys(Nicotinyl)-Leu-Lys(N-epsilon-Isopropyl)-Pro-DGlu}-NH₂
Ac-D1Nal-D4ClPhe-c-{DLys-Ser-NMeTyr-DLys(Nicotinyl)-Leu-Lys(N-epsilon-Isopropyl)-Pro-DGlu}-NH₂

EXAMPLE 23

Using the procedure described in Example 22, but substituting Boc-DPhe instead of Boc-D4ClPhe, the following compounds are obtained:

Ac-D2Nal-DPhe-c-{DLys-Ser-NMeTyr-DLys(Nicotinyl)-Leu-Lys(N-epsilon-Isopropyl)-Pro-DGlu}-NH₂
Ac-D3Qal-DPhe-c-{DLys-Ser-NMeTyr-DLys(Nicotinyl)-Leu-Lys(N-epsilon-Isopropyl)-Pro-DGlu}-NH₂
Ac-D4ClPhe-DPhe-c-{DLys-Ser-NMeTyr-DLys(Nicotinyl)-Leu-Lys(N-epsilon-Isopropyl)-Pro-DGlu}-NH₂
Ac-DPhe-DPhe-c-{DLys-Ser-NMeTyr-DLys(Nicotinyl)-Leu-Lys(N-epsilon-Isopropyl)-Pro-DGlu}-NH₂
Ac-D1Nal-DPhe-c-{DLys-Ser-NMeTyr-DLys(Nicotinyl)-Leu-Lys(N-epsilon-Isopropyl)-Pro-DGlu}-NH₂

EXAMPLE 24

Using the procedure described in Example 23, but substituting Boc-D2Nal instead of Boc-DPhe, the following compounds are obtained:

Ac-D2Nal-D2Nal-c-{DLys-Ser-NMeTyr-DLys(Nicotinyl)-Leu-Lys(N-epsilon-Isopropyl)-Pro-DGlu}-NH₂
Ac-D3Qal-D2Nal-c-{DLys-Ser-NMeTyr-DLys(Nicotinyl)-Leu-Lys(N-epsilon-Isopropyl)-Pro-DGlu}-NH₂
Ac-D4ClPhe-D2Nal-c-{DLys-Ser-NMeTyr-DLys(Nicotinyl)-Leu-Lys(N-epsilon-Isopropyl)-Pro-DGlu}-NH₂
Ac-DPhe-D2Nal-c-{DLys-Ser-NMeTyr-DLys(Nicotinyl)-Leu-Lys(N-epsilon-Isopropyl)-Pro-DGlu}-NH₂
Ac-D1Nal-D2Nal-c-{DLys-Ser-NMeTyr-DLys(Nicotinyl)-Leu-Lys(N-epsilon-Isopropyl)-Pro-DGlu}-NH₂

EXAMPLE 25

Using the procedure described in Example 1, but substituting Boc-D4FPhe instead of Boc-D2Nal, the following compounds are obtained:

Ac-D2Nal-D4FPhe-c-{DLys-Ser-NMeTyr-DLys(Nicotinyl)-Leu-Lys(N-epsilon-Isopropyl)-Pro-DGlu}-NH₂

Ac-D3Qal-D4FPhe-c-{DLys-Ser-NMeTyr-DLys(Nicotinyl)-Leu-Lys(N-epsilon-Isopropyl)-Pro-DGlu}-NH<sub>2</sub>
Ac-D4ClPhe-D4FPhe-c-{(DLys-Ser-NMeTyr-DLys(Nicotinyl)-Leu-Lys(N-epsilon-Isopropyl)-Pro-DGlu}-NH<sub>2</sub>
Ac-DPhe-D4FPhe-c-{DLys-Ser-NMeTyr-DLys(Nicotinyl)-Leu-Lys-(N-epsilon-Isopropyl)-Pro-DGlu-56 -NH<sub>2</sub>
Ac-D1Nal-D4FPhe-c-{DLys-Ser-NMeTyr-DLys(Nicotinyl)-Leu-Lys(N-epsilon-Isopropyl)-Pro-DGlu}-NH<sub>2</sub>

EXAMPLE 26

Using the procedure described in Example 1, but substituting the appropriate Boc-amino acid instead of BOC-NMe-Tyr(O-2,6-diCl-Bzl), the following compounds are obtained:
Ac-D2Nal-D4ClPhe-c-{DLys-Ser-Arg-DLys(Nicotinyl)-Leu-Lys(N-epsilon-Isopropyl)-Pro-DGlu}-NH<sub>2</sub>
Ac-D2Nal-D4ClPhe-c-{DLys-Ser-Phe-DLys(Nicotinyl)-Leu-Lys(N-epsilon-Isopropyl)-Pro-DGlu}-NH<sub>2</sub>
Ac-D2Nal-D4ClPhe-c-{DLys-Ser-Tyr(OMe)-DLys(Nicotinyl)-Leu-Lys(N-epsilon-Isopropyl)-Pro-DGlu}-NH<sub>2</sub>
Ac-D2Nal-D4ClPhe-c-{DLys-Ser-Lys(Nic)-DLys(Nicotinyl)-Leu-Lys(N-epsilon-Isopropyl)-Pro-DGlu}-NH<sub>2</sub>
Ac-D2Nal-D4ClPhe-c-{DLys-Ser-Lys(Pic)-DLys(Nicotinyl)-Leu-Lys(N-epsilon-Isopropyl)-Pro-DGlu}-NH<sub>2</sub>

EXAMPLE 27

Using the procedure described in Example 1, but substituting the appropriate Boc-amino acid instead of BOC-D-Lys(N-epsilon-Nicotinyl), the following compounds are obtained:
Ac-D2Nal-D4ClPhe-c-{DLys-Ser-NMeTyr-DLys(Pyz)-Leu-Lys(N-epsilon-Isopropyl)-Pro-DGlu}-NH<sub>2</sub>
Ac-D2Nal-D4ClPhe-c-{DLys-Ser-NMeTyr-DLys(GlyNic)-Leu-Lys(N-epsilon-Isopropyl)-Pro-DGlu}-NH<sub>2</sub>
Ac-D2Nal-D4ClPhe-c-{DLys-Ser-NMeTyr-DCit-Leu-Lys(N-epsilon-Isopropyl)-Pro-DGlu}-NH<sub>2</sub>
Ac-D2Nal-D4ClPhe-c-{DLys-Ser-NMeTyr-DHCit-Leu-Lys(N-epsilon-Isopropyl)-Pro-DGlu}-NH<sub>2</sub>
Ac-D2Nal-D4ClPhe-c-{DLys-Ser-NMeTyr-DLys(6ANic)-Leu-Lys(N-epsilon-Isopropyl)-Pro-DGlu}-NH<sub>2</sub>
Ac-D2Nal-D4ClPhe-c-{DLys-Ser-NMeTyr-DHArg(Et<sub>2</sub>)-Leu-Lys(N-epsilon-Isopropyl)-Pro-DGlu}-NH<sub>2</sub>

EXAMPLE 28

Using the procedure described in Example 1, but substituting the appropriate Boc-amino acid instead of BOC-Leu, the following compounds can be obtained:
Ac-D2Nal-D4ClPhe-c-{DLys-Ser-NMeTyr-DLys(Nicotinyl)-NMeLeu-Lys(N-epsilon-Isopropyl)-Pro-DGlu}-NH<sub>2</sub>
Ac-D2Nal-D4ClPhe-c-{DLys-Ser-NMeTyr-DLys(Nicotinyl)-ILe-Lys(N-epsilon-Isopropyl)-Pro-DGlu}-NH<sub>2</sub>
Ac-D2Nal-D4ClPhe-c-{DLys-Ser-NMeTyr-DLys(Nicotinyl)-Val-Lys(N-epsilon-Isopropyl)-Pro-DGlu}-NH<sub>2</sub>

EXAMPLE 29

Using the procedure described in Example 1, but substituting the appropriate Boc-amino acid instead of BOC-Lys(N-epsilon-Cbz,Isopropyl), the following compounds are obtained:
Ac-D2Nal-D4ClPhe-c-{DLys-Ser-NMeTyr-DLys(Nicotinyl)-Leu-HArg-Pro-DGlu}-NH<sub>2</sub>
Ac-D2Nal-D4ClPhe-c-{DLys-Ser-NMeTyr-DLys(Nicotinyl)-Leu-HArg(Et<sub>2</sub>)-Pro-DGlu}-NH<sub>2</sub>
Ac-D2Nal-D4ClPhe-c-{DLys-Ser-NMeTyr-DLys(Nicotinyl)-Leu-Arg-Pro-DGlu}-NH<sub>2</sub>
Ac-D2Nal-D4ClPhe-c-{DLys-Ser-NMeTyr-DLys(Nicotinyl)-Leu-HCit-Pro-DGlu}-NH<sub>2</sub>

EXAMPLE 30

Using the procedure described in Example 1, but substituting the appropriate Boc-amino acid instead of BOC-Pro, the following compounds are obtained:
Ac-D2Nal-D4ClPhe-c-{DLys-Ser-NMeTyr-DLys(Nicotinyl)-Leu-Lys(N-epsilon-Isopropyl)-NMeAla-DGlu}-NH<sub>2</sub>
Ac-D2Nal-D4ClPhe-c-{DLys-Ser-NMeTyr-DLys(Nicotinyl)-Leu-Lys(N-epsilon-Isopropyl)-Gly-DGlu}-NH<sub>2</sub>
Ac-D2Nal-D4ClPhe-c-{DLys-Ser-NMeTyr-DLys(Nicotinyl)-Leu-Lys(N-epsilon-Isopropyl)-Sar-DGlu}-NH<sub>2</sub>

EXAMPLE 31

Using the procedure described in Example 26, but substituting Boc-Phe(4NFMOC) for BOC-NMe-Tyr(O-2,6-diCl-Bzl) yields a peptide-resin which is treated with with 30% piperidine in DMF for 2 hr, washed three times with (1:1) DMF/DCM, treated with a solution of diphenyl cyanocarbonimidate in DMF and mixed for 16 hr. The resin is then washed three times each with DCM/DMF, MeOH, and DCM, and treated with excess hydrazine in dimethylformamide (DMF) for 8 hr. The resin is then washed as previously described and dried in vacuo overnight over P<sub>2</sub>O<sub>5</sub>. After HF treatment, lyophilization, cyclization, workup, and HPLC purification Ac-D2Nal-D4ClPhe-c-{DLys-Ser-Phe(Atz)-DLys(Nicotinyl)-Leu-Lys(N-epsilon-Isopropyl)-Pro-DGlu}-NH<sub>2</sub> is obtained.

EXAMPLE 32

Using the procedure described in Example 27, but substituting Boc-D-Phe(4NFMOC) for BOC-D-Lys(N-epsilon-Nicotinyl) yields a peptide-resin which is treated with with 30% piperidine in DMF for 2 hr, washed three times with (1:1) DMF/DCM, treated with a solution of diphenyl cyanocarbonimidate in DMF and mixed for 16 hr. The resin is then washed three times each with DCM/DMF, MeOH, and DCM, and treated with excess hydrazine in DMF for 8 hr. The resin is then washed as previously described and dried in vacuo overnight over P<sub>2</sub>O<sub>5</sub>. After HF treatment, lyophilization, cyclization, workup, and HPLC purification Ac-D2Nal-D4ClPhe-c-{DLys-Ser-NMeTyr-DLys(Atz)-Leu-Lys(N-epsilon-Isopropyl)-Pro-DGlu}-NH<sub>2</sub> is obtained.

EXAMPLE 33

Using the procedure described in Example 26, but substituting Boc-NMe-Phe(4NFMOC) for BOC-NMe-Tyr(O-2,6-diCl-Bzl) yields a peptide-resin which is treated with with 30% piperidine in DMF for 2 hr, washed three times with (1:1) DMF/DCM, treated with a solution of diphenyl cyanocarbonimidate in DMF and mixed for 16 hr. The resin is then washed three times each with DCM/DMF, MeOH, and DCM, and treated with hydrazine for 8 hr. The resin is then washed as previously described and dried in vacuo overnight over P<sub>2</sub>O<sub>5</sub>. After HF treatment, lyophilization, cyclization, workup, and HPLC purification Ac-D2Nal-D4ClPhe-c-{DLys-Ser-NMePhe(Atz)-DLys(Nicotinyl)-Leu-Lys(N-epsilon-Isopropyl)-Pro-DGlu}-NH<sub>2</sub> is obtained.

EXAMPLE 34

Using the procedure described in Example 1, but substituting BOC-DLys(N-epsilon-FMOC) for the BOC-DLys(N-epsilon-nicotinyl) used there, yields a peptide resin which is treated with 30% piperidine in DMF solution for 4 to 24 hours to remove the FMOC protecting group. After several washes with methylene chloride the peptide resin is treated with a solution of carbonyldiimidazole in DMF for 15 minutes, washed three times with methylene chloride, then reacted overnight with a solution of nicotinic hydrazide in DMF (18 ml). After HF treatment, lyophilization, cyclization, workup, and HPLC purification, Ac-D2Nal-D4ClPhe-c-{ DLys-Ser-NMeTyr-DLys(AzaGlyNic)-Leu-Lys(N-epsilon-Isopropyl)-NMeAla-DGlu}-NH$_2$ is obtained.

EXAMPLE 35

Using the procedure described in Example 1, but substituting BOC-DLys(N-epsilon-FMOC) for the BOC-DLys(N-epsilon-nicotinyl) used there, yields a peptide resin which is treated with 30% piperdine in DMF solution for 4 to 24 hours to remove the FMOC protecting group. After several washes with methylene chloride the peptide resin is treated with a solution of carbonyldiimidazole in DMF for 15 minutes, washed three times with methylene chloride, then reacted overnight with a solution of 2-furoic hydrazide in DMF. After HF treatment, lyophilization, cyclization, workup, and HPLC purification, Ac-D2Nal-D4ClPhe-c-{ DLys-Ser-NMeTyr-DLys(FurAzaGly)-Leu-Lys(N-epsilon-Isopropyl)-NMeAla-DGlu}-NH$_2$ is obtained.

We claim:

1. A cyclic peptide antagonist of LHRH or a pharmaceutically acceptable salt thereof selected from the group consisting of:

AcD2Nal-D4ClPhe-c-{DLys-Ser-NMeTyr-DLys(Nicotinyl)-Leu-Lys(N-epsilon-Isopropyl)-Pro-DGlu}-NH$_2$;
AcD2Nal-D4ClPhe-c-{DLys-Ser-Tyr-DLys(Nicotinyl)-Leu-Lys(N-epsilon-Isopropyl)-Pro-Glu}-NH$_2$;
AcD2Nal-D4ClPhe-c-{Lys-Ser-NMeTyr-DLys(Nicotinyl)-Leu-Lys(N-epsilon-Isopropyl)-Pro-DGlu}-NH$_2$;
AcD2Nal-D4ClPhe-c-{DLys-Ser-NMeTyr-DLys(Nicotinyl)-Leu-Lys(N-epsilon-Isopropyl)-Pro-Glu}-NH$_2$;
AcD2Nal-D4ClPhe-c-{Lys-Ser-NMeTyr-DLys(Nicotinyl)-Leu-Lys(N-epsilon-Isopropyl)-Pro-Glu}-NH$_2$;
AcD2Nal-D4ClPhe-c-{Glu-Ser-NMeTyr-DLys(Nicotinyl)-Leu-Lys(N-epsilon-Isopropyl)-Pro-DOrn}-NH$_2$;
AcD2Nal-D4ClPhe-c-{DGlu-Ser-NMeTyr-DLys(Nicotinyl)-Leu-Lys(N-epsilon-Isopropyl)-Pro-DLys}-NH$_2$;
AcD2Nal-D4ClPhe-c-{DLys-Ser-Tyr-DLys(Nicotinyl)-Leu-Lys(N-epsilon-Isopropyl)-Pro-DGlu}-NH$_2$;
4F-Phenylacetyl-c-{DLys-Ser-NMeTyr-DLys(Nicotinyl)-Leu-Lys(N-epsilon-Isopropyl)-Pro-DGlu}-NH$_2$;
Ac-c-{DGlu-Ser-NMeTyr-DLys(Nicotinyl)-Leu-Lys(N-epsilon-Isopropyl)-Pro-DLys}-NH$_2$;
AcD2Nal-D4ClPhe-c-{DGlu-Ser-NMeTyr-DLys(Nicotinyl)-Leu-Lys(N-epsilon-Isopropyl)-Pro-DGlu}-NH$_2$;
4-ClPhenylpropionyl-c-{DLys-Ser-NMeTyr-DLys(Nicotinyl)-Leu-Lys(N-epsilon-Isopropyl)-Pro-DGlu}-NH$_2$;
AcD2Nal-D4ClPhe-c-{DOrn-Ser-NMeTyr-DLys(Nicotinyl)-Leu-Lys(N-epsilon-Isopropyl)-Pro-DGlu}-NH$_2$;
4Cl-Phenylpropionyl-c-{DLys-Ser-NMeTyr-DLys(Nicotinyl)-Leu-Lys(N-epsilon-Isopropyl)-Gly-DGlu}-NH$_2$;
AcD2Nal-D4ClPhe-c-{DLys-Gly-NMeTyr-DLys(Nicotinyl)-Leu-Lys(N-epsilon-Isopropyl)-Gly-DGlu}-NH$_2$;
Ac-c-{DLys-Ser-NMeTyr-DLys(Nicotinyl)-Leu-Lys(N-epsilon-Isopropyl)-Pro-DGlu}-NH$_2$.

* * * * *

UNITED STATES PATENT AND TRADEMARK OFFICE
CERTIFICATE OF CORRECTION

PATENT NO. : 5,508,383
DATED : April 16, 1996
INVENTOR(S) : F. Haviv and d. Sauer It is certified that error appears in the above-indentified patent and that said Letters Patent is hereby corrected as shown below:

Column 22, line 22, change "Pro-DGlu" to --Pro-Lys--.

Column 22, line 30-31, insert --and-- between "NH$_2$;" and "Ac-c".

Signed and Sealed this

Twenty-fifth Day of March, 1997

Attest:

BRUCE LEHMAN

Attesting Officer

Commissioner of Patents and Trademarks